(12) United States Patent
Duncan

(10) Patent No.: US 10,005,790 B2
(45) Date of Patent: Jun. 26, 2018

(54) PROCESS FOR THE SYNTHESIS OF SUBSTITUTED MORPHINANS

(71) Applicant: Alkermes Pharma Ireland Limited, Dublin (IE)

(72) Inventor: Scott Duncan, Bedford, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 248 days.

(21) Appl. No.: 14/199,371

(22) Filed: Mar. 6, 2014

(65) Prior Publication Data

US 2014/0303371 A1    Oct. 9, 2014

Related U.S. Application Data

(63) Continuation of application No. 13/096,679, filed on Apr. 28, 2011, now abandoned.

(60) Provisional application No. 61/362,388, filed on Jul. 8, 2010.

(51) Int. Cl.
   *C07D 489/08* (2006.01)
   *C07D 491/18* (2006.01)
   *C07D 491/20* (2006.01)

(52) U.S. Cl.
   CPC ......... *C07D 489/08* (2013.01); *C07D 491/20* (2013.01)

(58) Field of Classification Search
   CPC .......................... C07D 491/18; C07D 489/08
   USPC ...................................................... 546/15, 39
   See application file for complete search history.

(56) References Cited

FOREIGN PATENT DOCUMENTS

| BE | 634402 A1 | 1/1963 |
| GB | 981046 A | 1/1965 |
| JP | 5231100 A | 3/1977 |
| WO | 2004005294 A2 | 1/2004 |
| WO | 2008048711 A1 | 4/2008 |
| WO | 2009009083 A1 | 1/2009 |
| WO | WO 2009/023567 A1 * | 2/2009 |

OTHER PUBLICATIONS

Wentland, M. et al. Syntheses of novel high affinity ligands for opioid receptors. Bioorganic & Medicinal Chemistry Letters. 2009, vol. 19, p. 2290.*
Kocienski, PJ. et al. Protecting Groups. Thieme. 2005, p. 50.*
Wentland, M. et al. Syntheses and opioid receptor binding properties of carboxamido-substituted opioids. Bioorganic & Medicinal Chemistry Letters. 2009, vol. 19, p. 204.*
Tada, H., et al., "Ketalisation of alpha, beta-Unsaturated Ketones: Part I 3-Methoxy-N-Methylmorphinan Derivatives and 14-Hydroxcodeinone," Tetrahedron Letters, 10(22): pp. 1805-1808 (1969).
Kubota, H., et al., "Palladium-Catalyzed Cyanation of Hindered, Electron-Rich Aryl Triflates by Zinc Cyanide," Tetrahedron Letters 39: pp. 2907-2910 (1998).

* cited by examiner

*Primary Examiner* — Charanjit Aulakh
(74) *Attorney, Agent, or Firm* — Elmore Patent Law Group, P.C.; Joseph Zucchero; Carolyn Elmore

(57) ABSTRACT

The present invention relates to compounds of formula I and a process for the synthesis:

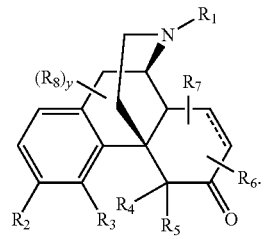

The invention further relates to a process for the synthesis of 3-carboxamide substituted morphinans where a 3-cyano substituted 6-oxo substituted morphinan is reacted with a 1,3-diol.

8 Claims, No Drawings

PROCESS FOR THE SYNTHESIS OF SUBSTITUTED MORPHINANS

RELATED APPLICATIONS

This application is a continuation of U.S. application Ser. No. 13/096,679, filed Apr. 28, 2011 which claims the benefit of U.S. Provisional Application No. 61/362,388, filed on Jul. 8, 2010. The entire teachings of the above application are incorporated herein by reference.

BACKGROUND OF THE INVENTION

Opiates have been the subject of intense research since the isolation of morphine in 1805, and thousands of compounds having opiate or opiate-like activity have been identified. Many opioid receptor-interactive compounds including those used for producing analgesia (e.g., morphine) and those used for treating drug addiction (e.g., naltrexone and cyclazocine) in humans have limited utility due to poor oral bioavailability and a very rapid clearance rate from the body. This has been shown in many instances to be due to the presence of the 8-hydroxyl group (OH) of 2,6-methano-3-benzazocines, also known as benzomorphans [(e.g., cyclazocine and EKC (ethylketocyclazocine)] and the corresponding 3-OH group in morphinans (e.g., morphine).

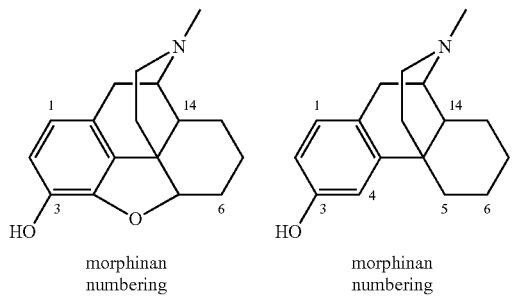

morphinan numbering morphinan numbering

Recently morphinans have received renewed attention for the treatment of opioid mediated diseases since the conversion of phenolic C-3 hydroxyl to a carboxamide moiety has been found to improve their bioavailability. (U.S. Pat. Nos. 6,784,187; 6,887,998; 7,265,226; 7,057,035; 7,262,298; U.S. Patent Publication No. 20070021457). However, challenges to producing carboxamide substituted morphinans, particularly in large scale processes, remain.

A common method for the synthesis of carboxamide substituted morphinans involves the conversion of morphinans with C-3-hydroxyl group to a triflate group followed by palladium catalyzed replacement of triflate with cyanide group, and conversion of the cyanide group to a carboxamide group. Wentland et al., *Selective Protection and Functionalization of Morphine: Synthesis and Opioid Receptor Binding Properties of 3-Amino-3-desoxymorphine Derivatives*, J. Med. Chem., 2000, 43 (19), pp 3558-3565. However, the use of reagents such as triflic anhydride to convert the hydroxyl to a triflate group often leads to side reactions if other functional groups are present. Such side reactions lead to lower yields and make the purification process cumbersome. Furthermore, milder reagents such as N-phenylbis(trifluoromethanesulfonimide) are not suitable for large scale synthesis since such reagents are generally expensive and require laborious processing to remove the by-products that they produce. As such, new methods for synthesizing substituted morphinans, particularly carboxamide substituted morphinans are needed.

SUMMARY OF THE INVENTION

In part, the invention provides a multistep process for the synthesis of a compound of formula I:

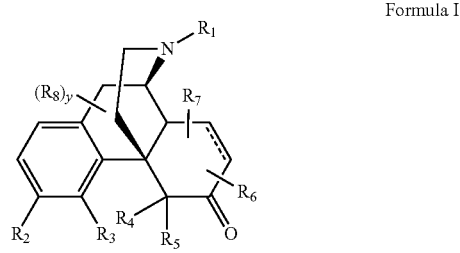

Formula I or a pharmaceutically acceptable salt, ester or prodrug thereof wherein;

$R_1$ is chosen from hydrogen, halogen, optionally substituted aliphatic, optionally substituted aryl or optionally substituted heterocyclyl;

$R_2$ is $-CON(R_{20})(R_{21})$ or $-CSN(R_{20})(R_{21})$, wherein each $R_{20}$ and $R_{21}$ is independently selected from hydrogen, halogen, optionally substituted aliphatic, optionally substituted aryl or optionally substituted heterocyclyl; alternatively, $R_{20}$ and $R_{21}$ together with the nitrogen to which they are attached to forms a heterocyclic ring;

$R_3$ and $R_4$ are independently H, $-OH$, $-SH$, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl; or together $R_3$ and $R_4$ form an $-O-$ or $-S-$ group;

Each $R_5$, $R_6$, $R_7$, and $R_8$ is independently hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl;

y is 0, 1 or 2.

Step 1 relates to the conversion of a compound of formula IA or a salt or hydrate thereof to a compound of formula IB or a salt or hydrate thereof:

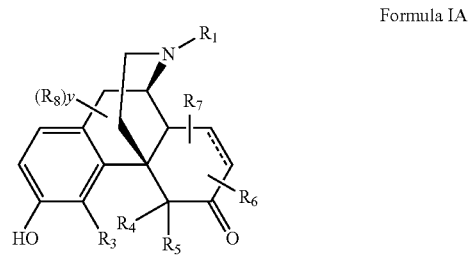

Formula IA

Formula IB

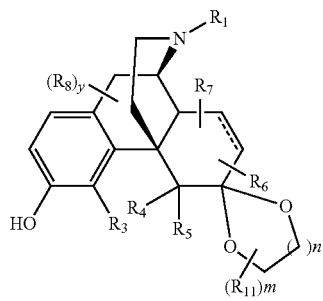

wherein, $R_1$, $R_3$, $R_4$, $R_5$, $R_6$, $R_7$, and $R_8$ are as defined above;

Each $R_{11}$ is independently, hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino or optionally substituted $C_1$-$C_8$ aryl; and Each m and n is an integer selected from 0, 1, 2, 3, 4, 5, 6, 7 or 8.

Step 2 relates to the conversion of a compound of formula IB or a salt or hydrate thereof to a compound of formula IC or a salt or hydrate thereof:

Formula IC

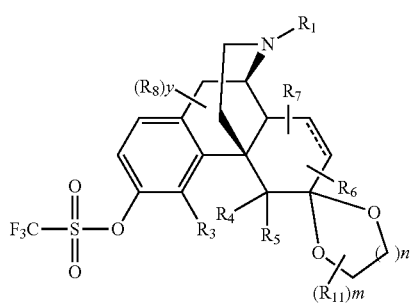

Step 3 relates to the conversion of a compound of formula IC or a salt or hydrate thereof to a compound of formula ID or a salt or hydrate thereof:

Formula ID

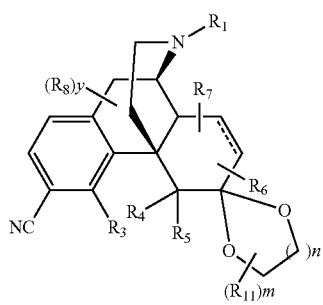

Step 4 relates to the conversion of a compound of formula ID or a salt or hydrate thereof to a compound of formula IE or a salt or hydrate thereof:

Formula IE

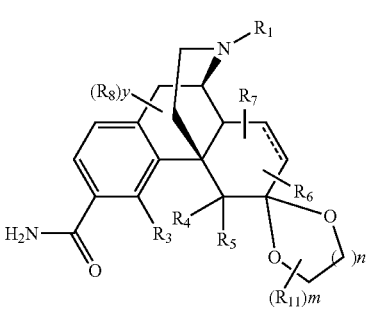

Step 5 relates to the conversion of a compound of formula IE or a salt or hydrate thereof to a compound of formula I or a salt or hydrate thereof.

DETAILED DESCRIPTION OF THE INVENTION

In part, the invention provides a multistep process for the synthesis of a compound of formula I:

Formula I

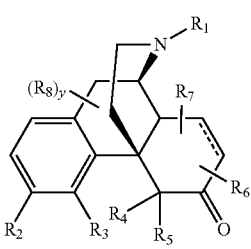

or a pharmaceutically acceptable salt or hydrate thereof wherein;

$R_1$ is chosen from hydrogen, halogen, optionally substituted aliphatic, optionally substituted aryl or optionally substituted heterocyclyl.

In a preferred embodiment, $R_1$ is selected from —$CH_3$, —$CH_2$-c-$C_3H_5$, —$CH_2$-c-$C_4H_7$, —$CH_2$—CH═$CH_2$, —$CH_2$—CH═$C(CH_3)_2$.

$R_2$ is —$CON(R_{20})(R_{21})$ or —$CSN(R_{20})(R_{21})$, wherein each $R_{20}$ and $R_{21}$ is independently hydrogen, halogen, optionally substituted aliphatic, optionally substituted aryl or optionally substituted heterocyclyl;

$R_3$ and $R_4$ are independently H, —OH, —SH, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl; or together $R_3$ and $R_4$ form an —O— or —S— group;

Each $R_5$, $R_6$, $R_7$, and $R_8$ is independently hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino and optionally substituted $C_1$-$C_8$ aryl; and y is 0, 1 or 2.

Step 1 relates to the conversion of a compound of formula IA or a salt or hydrate thereof to a compound of formula IB or a salt or hydrate thereof:

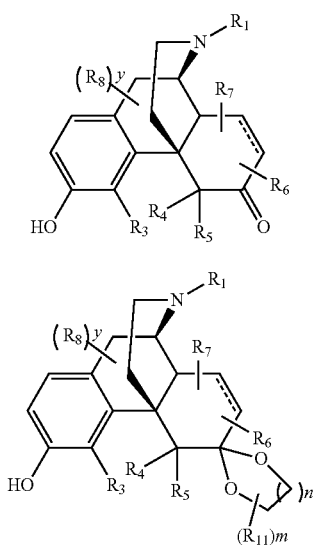

Formula IA

Formula IB

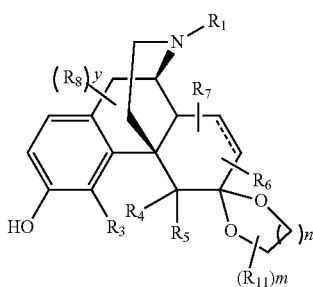

wherein, $R_1$, $R_3$, $R_4$, $R_5$, $R_6$, $R_7$, and $R_8$ are as defined above;
Each $R_{11}$ is independently, hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino or optionally substituted $C_1$-$C_8$ aryl; and
Each m and n is an integer selected from 0, 1, 2, 3, 4, 5, 6, 7 or 8.

Step 2 relates to the conversion of a compound of formula IB or a salt or hydrate thereof to a compound of formula IC or a salt or hydrate thereof:

Formula IC

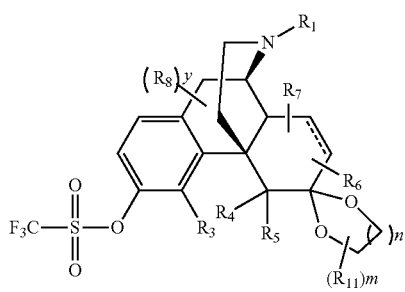

Step 3 relates to the conversion of a compound of formula IC or a salt or hydrate thereof to a compound of formula ID or a salt or hydrate thereof:

Formula ID

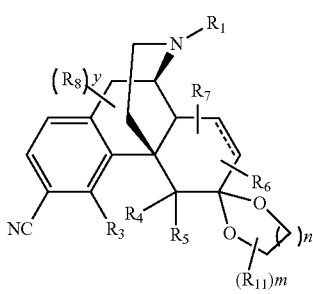

Step 4 relates to the conversion of a compound of formula ID or a salt or hydrate thereof to a compound of formula IE or a salt or hydrate thereof:

Formula IE

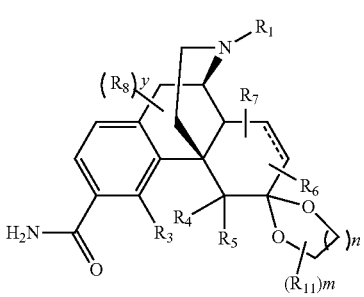

Step 5 relates to the conversion of a compound of formula IE or a salt or hydrate thereof to a compound of formula I or a salt or hydrate thereof.

The conversion of the phenolic oxygen in the opiate skeleton to other functionalities, such amines, ketones, amides and esters is plagued by the high reactivity of the C-6 ketone moiety under the transition metal catalyzed reactions that are typically used for these transformations. This leads to complex reaction mixtures requiring laborious and tedious purification techniques. These challenges result in increased production costs by requiring more expensive reagents, additional processing steps and increased cycle time resulting in lower yields.

One of the significant differences between synthesis through dioxalane and unprotected ketone is the physical form of the intermediates. The triflate intermediate is often an oil as the ketone analog. On the other hand, the ketal analogs of formula IC are generally solids. This allows a tedious and time consuming, and raw material intensive isolation and purification procedures to be replaced by precipitation of the intermediate. This reduces the processing costs and provides a pivotal intermediate with greater purity. The purity of this intermediate is a critical parameter for the subsequent step and downstream chemistry.

Step 1: Step 1 relates to the conversion of the C-6 carbonyl group to a 1,3 dioxalane group. A variety of methods are available to convert carbonyls to dioxalanes. (B. Karimi, B. Golshani, Synthesis, 2002, 784-788; H. Firouzabadi, N. Iranpoor, B. Karimi, Synlett, 1999, 321-323; R. Gopinath, Sk. J. Hague, B. K. Patel, J. Org. Chem., 2002, 67, 5842-5845). In a preferred embodiment dioxolanes are prepared from carbonyl compounds with 1,3-propanediol or 1,2-ethanediol in the presence of a Brönsted or a Lewis acid catalyst. A preferred catalyst is selected from p-toluenesulfonic acid, tetrabutylammonium tribromide, zirconium tetrachloride and iodine.

Step 2: Step 2 relates to the conversion of C-3 hydroxyl group to a triflate group. A variety of triflating agents can be used for triflating the C-3 hydroxyl group. (Frantz et. al., Org. Lett., 2002, 4 (26), pp 4717-4718). A preferred triflating agent is selected from 4-Nitrophenyltriflate, N-phenyl bis(trifluoromethanesulfonimide, trifluoromethanesulfonic anhydride (triflic anhydride) and triflyl chloride. In a more preferred embodiment the triflating agent is triflic anhydride. In one embodiment, a base catalyst is used in the triflation step. A preferred base is selected from diisopropylethylamine, pyridine, N,N-dimethylaminopyridine, triethylamine and 2,6-di-t-butyl-4-methylpyridine.

Step 3: Step 3 relates to replacement of the triflate group with a nitrile group. In a preferred embodiment, a palladium (Pd(0)) catalyst is used along with a source of cyanide ions, such as zinc cyanide ($Zn(CN)_2$). A preferred Pd(0) catalyst for use in the displacement with zinc cyanide is selected from tetrakis(triphenylphosphine)palladium and Tris(dibenzylideneacetone)dipalladium ($Pd_2(dba)_3$). A preferred group of ligands for Pd(0) include 1,1'-bis(diphenylphosphino)ferrocene (DPPF) and 4,5-Bis(diphenylphosphino)-9,9-dimethylxanthene (xantphos). In the direct exchange with carbon monoxide and ammonia or an ammonia equivalent, the preferred Pd(0) catalyst is generated in situ from $Pd(OAc)_2$ or $PdCl_2$ and 1,1'-bis(diphenylphosphino)-ferrocene. In other embodiments, Pd(0) ligands include 1,1'-bis(diphenylphosphino)ferrocene (DPPF), 1,3-bis(diphenylphosphino)propane (DPPP), triphenylphosphine, 1,3-bis(diphenylphosphino)propane, 2,2'-bis(diphenylphosphino)-1,1'-binaphthyl (BINAP) and 4,5-Bis(diphenylphosphino)-9,9-dimethylxanthene (xantphos).

Step 4: Step 4 relates to the conversion of C-3 nitrile group to carboxamide group through hydrolysis. Hydrolysis of the nitrile group can be performed under either basic or acidic conditions. In a preferred embodiment, a mixture of t-butanol and potassium hydroxide are used.

Optional Step 4E: Step 4E relates to the conversion of C-3 carboxamide to a thiocarboxamide group. The preferred pentavalent phosphorus-sulfur reagents for converting carboxamides to thiocarboxamides are Lawesson's reagent and phosphorus pentasulfide. (U.S. Pat. No. 6,784,187).

Step 5: In step 5, the dioxalane group is converted to a carbonyl group. In a preferred embodiment, the dioxalane is converted to ketone by using a mineral acid such as hydrochloric acid, optionally in a solvent selected from toluene, benzene and xylene. Other preferred agents for converting dioxalane to carbonyl group include indium(III)trifluoromethanesulfonate, erbium triflate, cerium(III)triflate, sodium tetrakis(3,5-trifluoromethylphenyl)borate and iodine. (B. T. Gregg, et. al., *J. Org. Chem.*, 2007, 72, 5890-5893; R. Dalpozzo, et. al., *Synthesis*, 2004, 496-498; R. Dalpozzo, et. al., *J. Org. Chem.*, 2002, 67, 9093-9095).

A comparison between the dioxalane method disclosed herein and the method in which the ketone moiety is carried through steps 1-5 without protection indicates that the dioxalane method provides significant improvements in both yield and purity.

Method A:

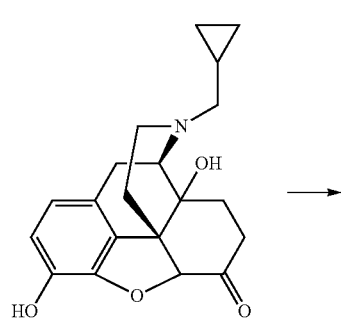

Method B:

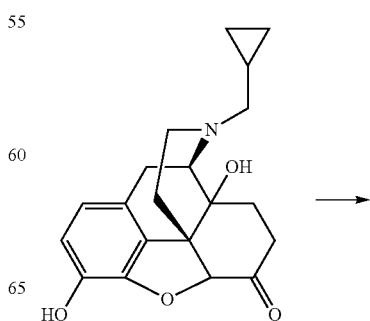

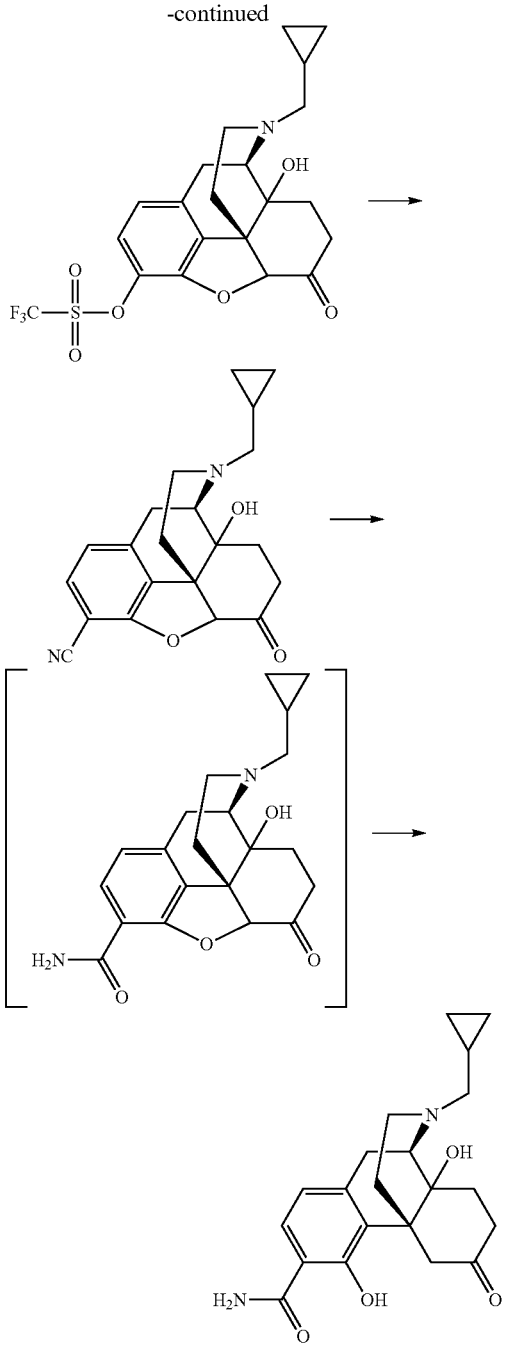

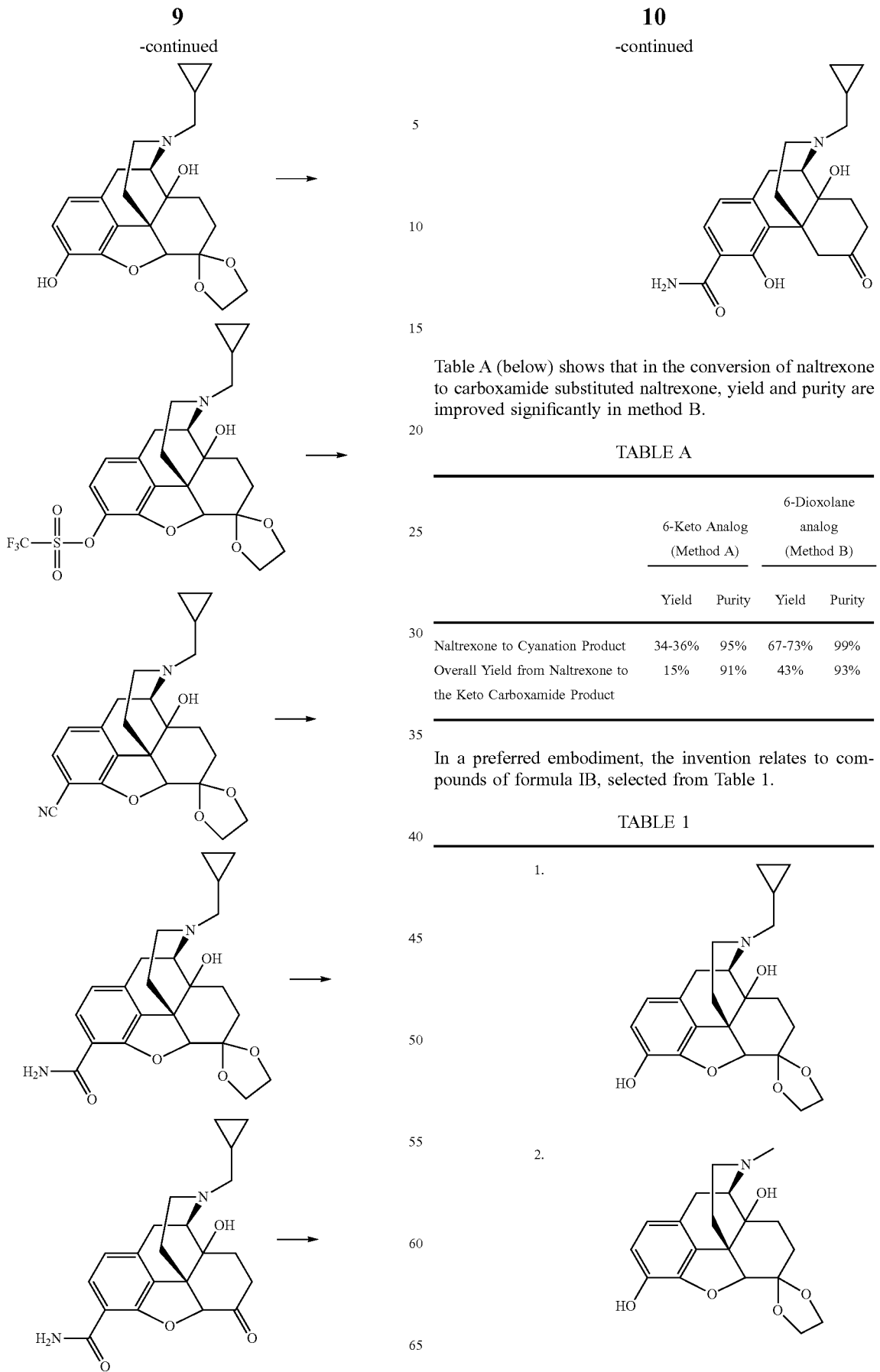

Table A (below) shows that in the conversion of naltrexone to carboxamide substituted naltrexone, yield and purity are improved significantly in method B.

TABLE A

|  | 6-Keto Analog (Method A) | | 6-Dioxolane analog (Method B) | |
| --- | --- | --- | --- | --- |
|  | Yield | Purity | Yield | Purity |
| Naltrexone to Cyanation Product | 34-36% | 95% | 67-73% | 99% |
| Overall Yield from Naltrexone to the Keto Carboxamide Product | 15% | 91% | 43% | 93% |

In a preferred embodiment, the invention relates to compounds of formula IB, selected from Table 1.

TABLE 1

TABLE 1-continued

3. [chemical structure]

4. [chemical structure]

5. [chemical structure]

6. [chemical structure]

7. [chemical structure]

TABLE 2

8. [chemical structure]

9. [chemical structure]

10. [chemical structure]

11. [chemical structure]

12. [chemical structure]

In a preferred embodiment, the invention relates to compounds of formula IC, selected from Table 2.

TABLE 2-continued
13. 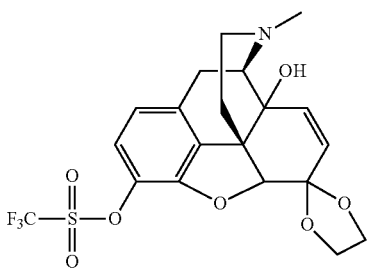 [SMILES: CN1CC[C@]23c4c5ccc(OS(=O)(=O)C(F)(F)F)c4OC2C2(C=CC3(O)[C@H]1C5)OCCO2]
14. 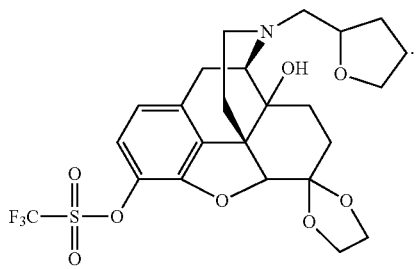 [SMILES: O=S(=O)(Oc1ccc2c3c1OC1C4(CCC5(O)[C@@H](C2)N(CC2CCCO2)CC[C@]315)OCCO4)C(F)(F)F]
In a preferred embodiment, the invention relates to compounds of formula ID, selected from Table 3.
TABLE 3
15. 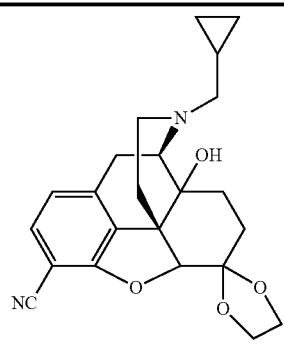
16. 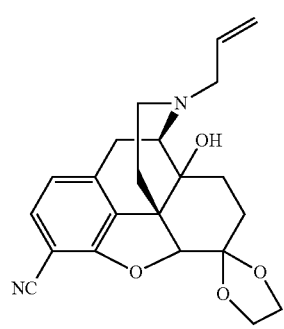 [SMILES: C=CCN1CC[C@]23c4c5ccc(C#N)c4OC2C2(CCC3(O)[C@H]1C5)OCCO2]
17. 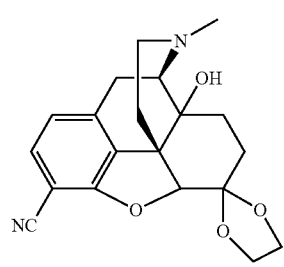 [SMILES: CN1CC[C@]23c4c5ccc(C#N)c4OC2C2(CCC3(O)[C@H]1C5)OCCO2]
TABLE 3-continued
18. 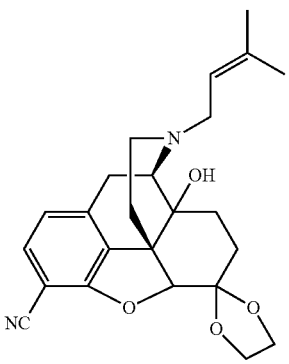 [SMILES: CC(C)=CCN1CC[C@]23c4c5ccc(C#N)c4OC2C2(CCC3(O)[C@H]1C5)OCCO2]
19. 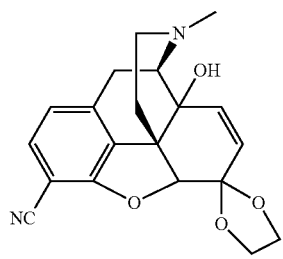 [SMILES: CN1CC[C@]23c4c5ccc(C#N)c4OC2C2(C=CC3(O)[C@H]1C5)OCCO2]
20. 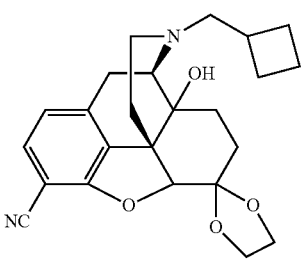 [SMILES: N#Cc1ccc2c3c1OC1C4(CCC5(O)[C@@H](C2)N(CC2CCC2)CC[C@]315)OCCO4]
21.
In a preferred embodiment, the invention relates to compounds of formula IE, selected from Table 4.
TABLE 4
22. 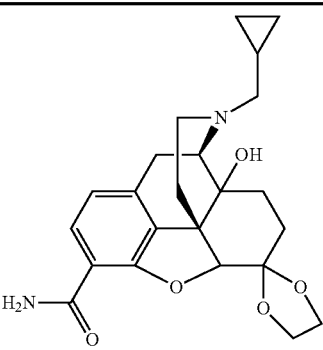

TABLE 4-continued
23. 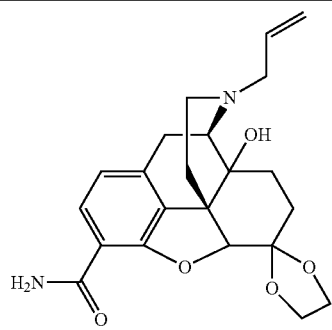
24. 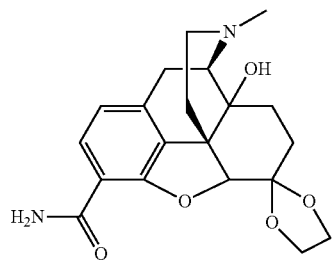 [SMILES: CN1CC[C@]23c4c5ccc(C(N)=O)c4OC2C2(CCC3(O)[C@H]1C5)OCCO2]
25. 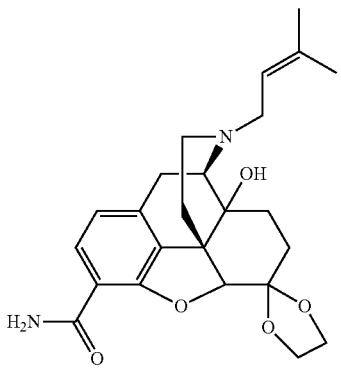 [SMILES: CC(C)=CCN1CC[C@]23c4c5ccc(C(N)=O)c4OC2C2(CCC3(O)[C@H]1C5)OCCO2]
26. 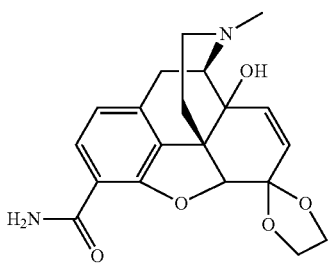 [SMILES: CN1CC[C@]23c4c5ccc(C(N)=O)c4OC2C2(C=CC3(O)[C@H]1C5)OCCO2]
27. 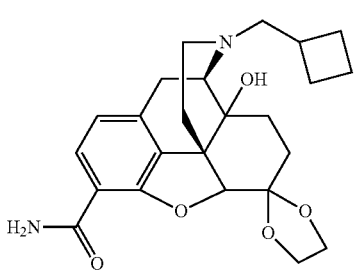 [SMILES: NC(=O)c1ccc2c3c1OC1C4(CCC5(O)[C@@H](C2)N(CC2CCC2)CC[C@]315)OCCO4]
28. 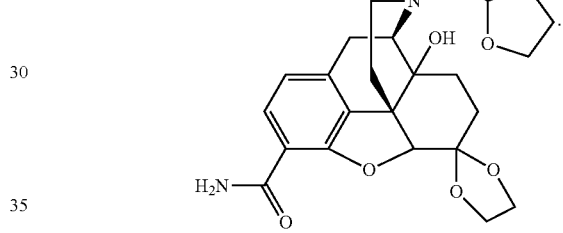
In another embodiment, the invention relates to a process for the synthesis of substituted morphinans as outlined in Method C:
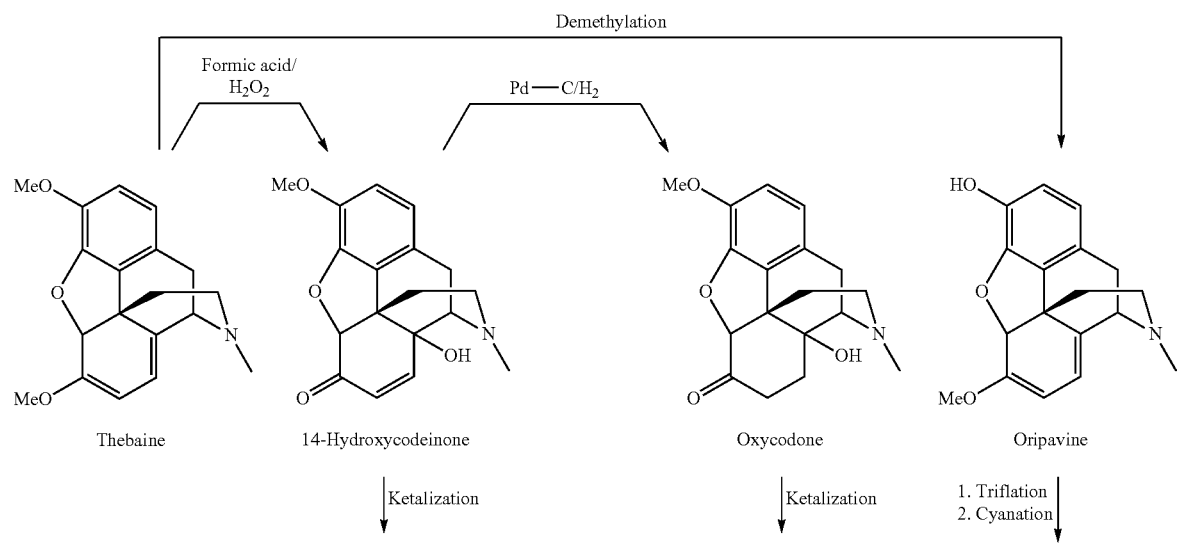

-continued

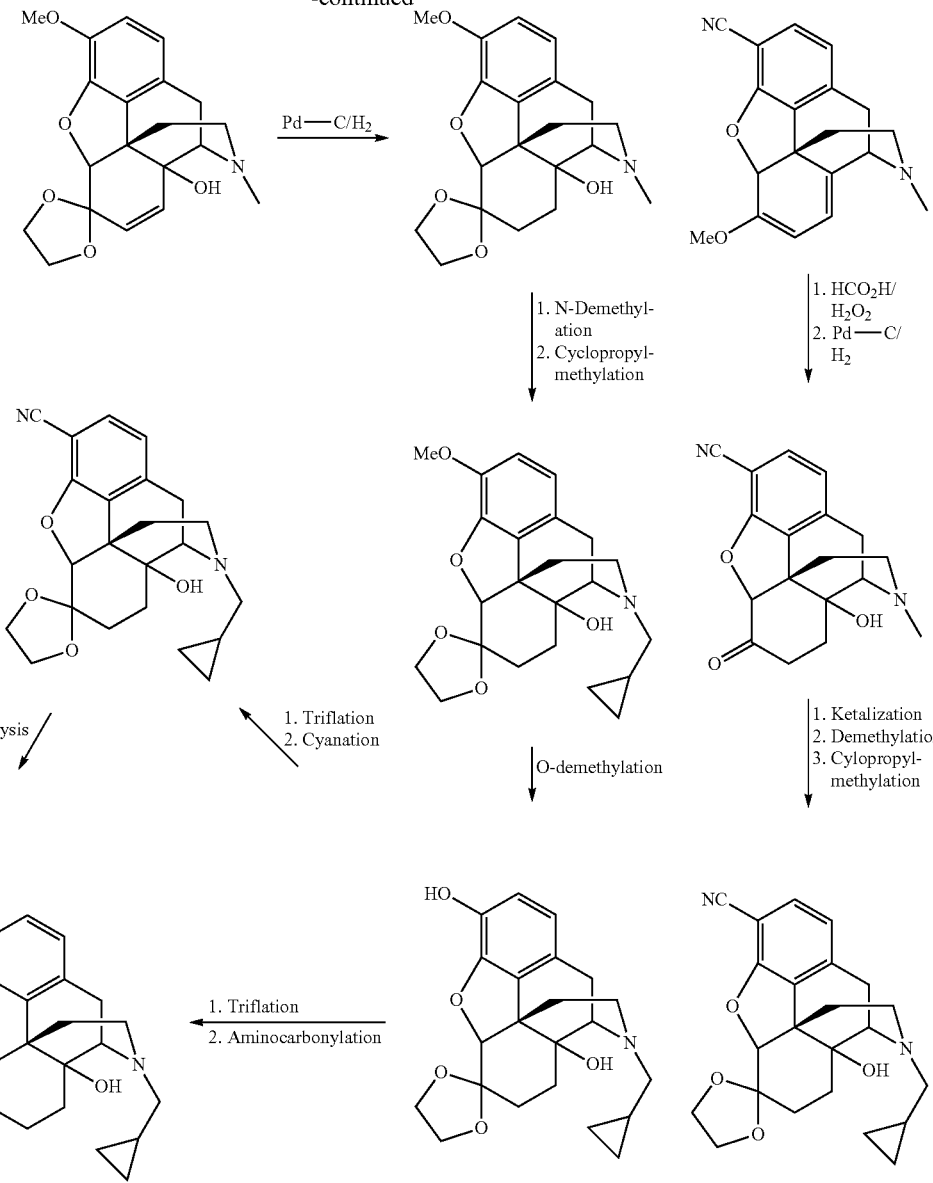

The invention further relates compounds of Formula IIB or a pharmaceutically acceptable salt or ester thereof, and their synthesis.

Formula IIB

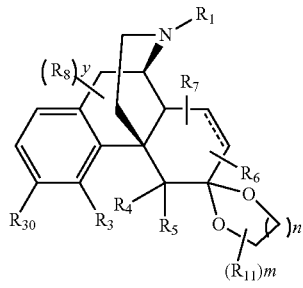

Wherein $R_1$, $R_3$, $R_4$, $R_5$, $R_6$, $R_7$, $R_8$, $R_{11}$, y, m, and n are as defined above;

$R_{30}$ is selected from hydrogen, halogen, —$OR_{20}$, —$SR_{20}$, —$NR_{20}R_{21}$, —$CF_3$, —CN, —$NO_2$, —$N_3$, —$C(O)OR_{20}$, —$C(O)R_{20}$, —$C(O)NR_2OR_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; Each $R_{11}$ is independently, hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_3$-$C_8$ cycloalkyl, optionally substituted $C_1$-$C_8$ alkoxy, optionally substituted $C_1$-$C_8$ alkylamino or optionally substituted $C_1$-$C_8$ aryl.

In a preferred embodiment, $R_{30}$ is selected from —$OR_{20}$ and —$SR_{20}$.

In one embodiment, the invention relates to the synthesis of a compound of Formula IIB comprising the step of reacting a compound of formula IIA:

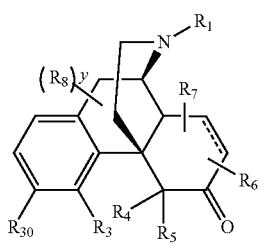

Formula IIA with a diol of the formula,

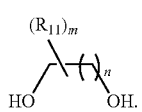

The above synthesis relates to the conversion of the C-6 carbonyl group to a 1,3 dioxalane group. A variety of methods are available to convert carbonyls to dioxalanes. (B. Karimi, B. Golshani, Synthesis, 2002, 784-788; H. Firouzabadi, N. Iranpoor, B. Karimi, Synlett, 1999, 321-323; R. Gopinath, Sk. J. Hague, B. K. Patel, J. Org. Chem., 2002, 67, 5842-5845). In a preferred embodiment dioxolanes are prepared from carbonyl compounds with 1,3-propanediol or 1,2-ethanediol in the presence of a Brönsted or a Lewis acid catalyst. A preferred catalyst is selected from p-toluenesulfonic acid, tetrabutylammonium tribromide, zirconium tetrachloride and iodine.

In a preferred embodiment, $R_1$ is selected from —$CH_3$, —$CH_2$-c-$C_3H_5$, —$CH_2$-c-$C_4H_7$, —$CH_2$—CH=$CH_2$, —$CH_2$—CH=$C(CH_3)_2$.

In a preferred embodiment, the compound of Formula IIB is selected from Table 5:

TABLE 5

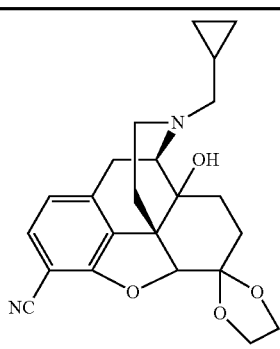

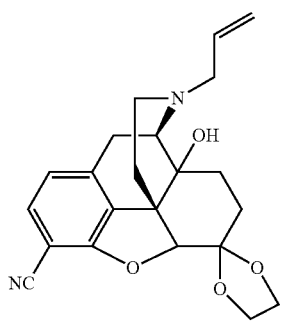 [SMILES: C=CCN1CC[C@]23c4c5ccc(C#N)c4OC2C2(CCC3(O)[C@H]1C5)OCCO2]

TABLE 5-continued

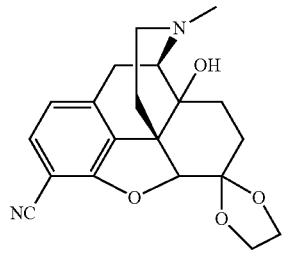 [SMILES: CN1CC[C@]23c4c5ccc(C#N)c4OC2C2(CCC3(O)[C@H]1C5)OCCO2]

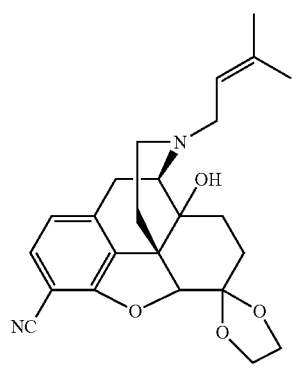 [SMILES: CC(C)=CCN1CC[C@]23c4c5ccc(C#N)c4OC2C2(CCC3(O)[C@H]1C5)OCCO2]

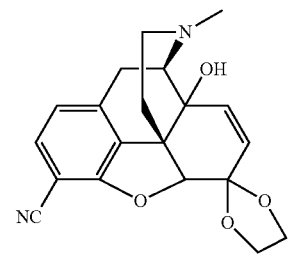 [SMILES: CN1CC[C@]23c4c5ccc(C#N)c4OC2C2(C=CC3(O)[C@H]1C5)OCCO2]

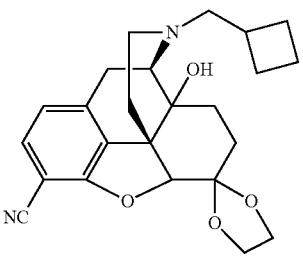 [SMILES: N#Cc1ccc2c3c1OC1C4(CCC5(O)[C@@H](C2)N(CC2CCC2)CC[C@]315)OCCO4]

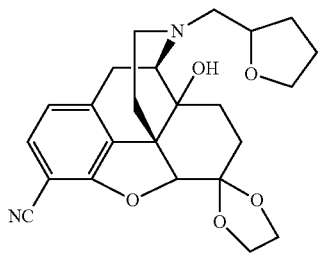 [SMILES: N#Cc1ccc2c3c1OC1C4(CCC5(O)[C@@H](C2)N(CC2CCCO2)CC[C@]315)OCCO4]

TABLE 5-continued
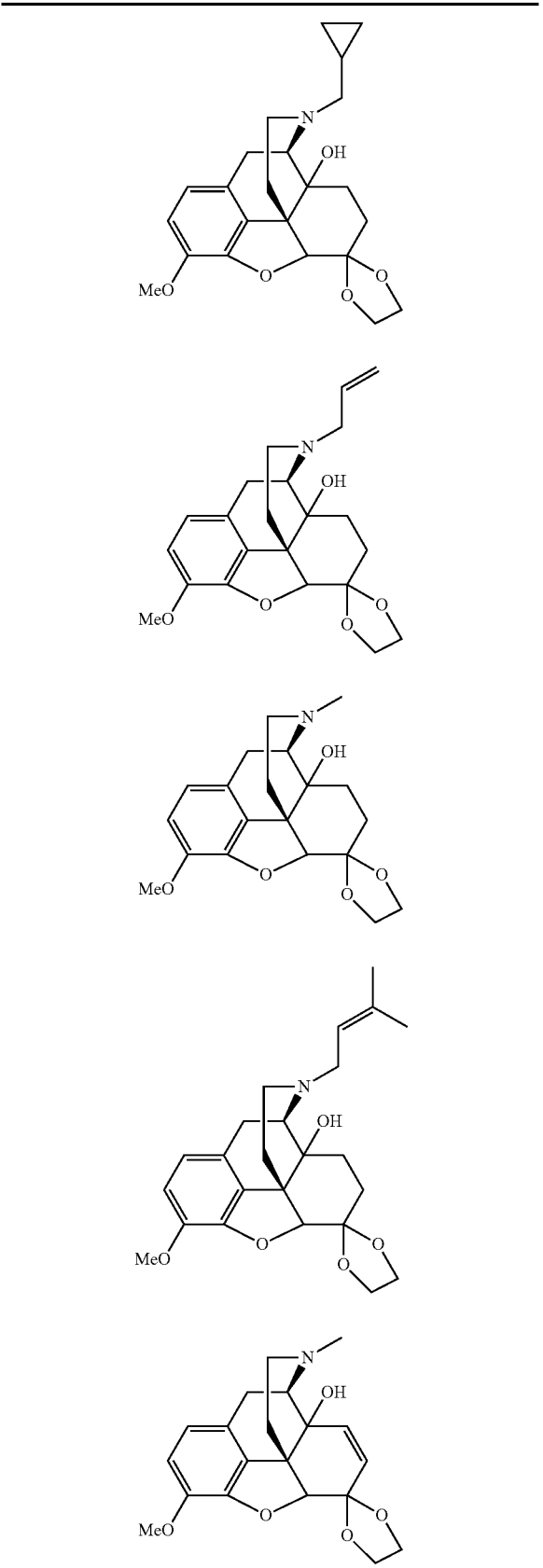
TABLE 5-continued
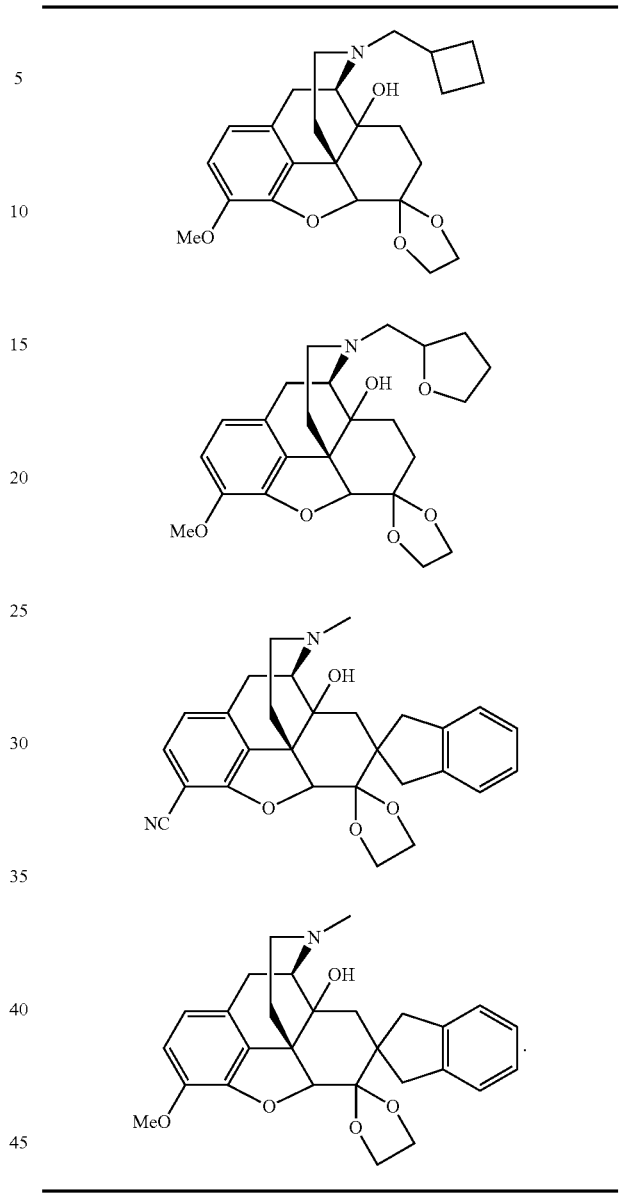
In a preferred embodiment, compound of Formula IIA is selected from Table 6:
TABLE 6
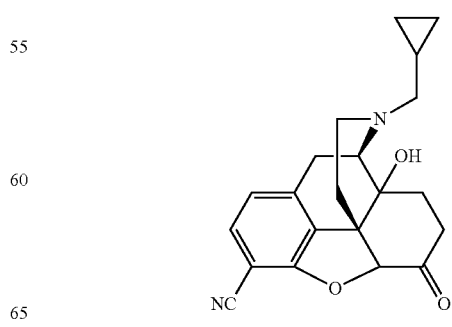

TABLE 6-continued
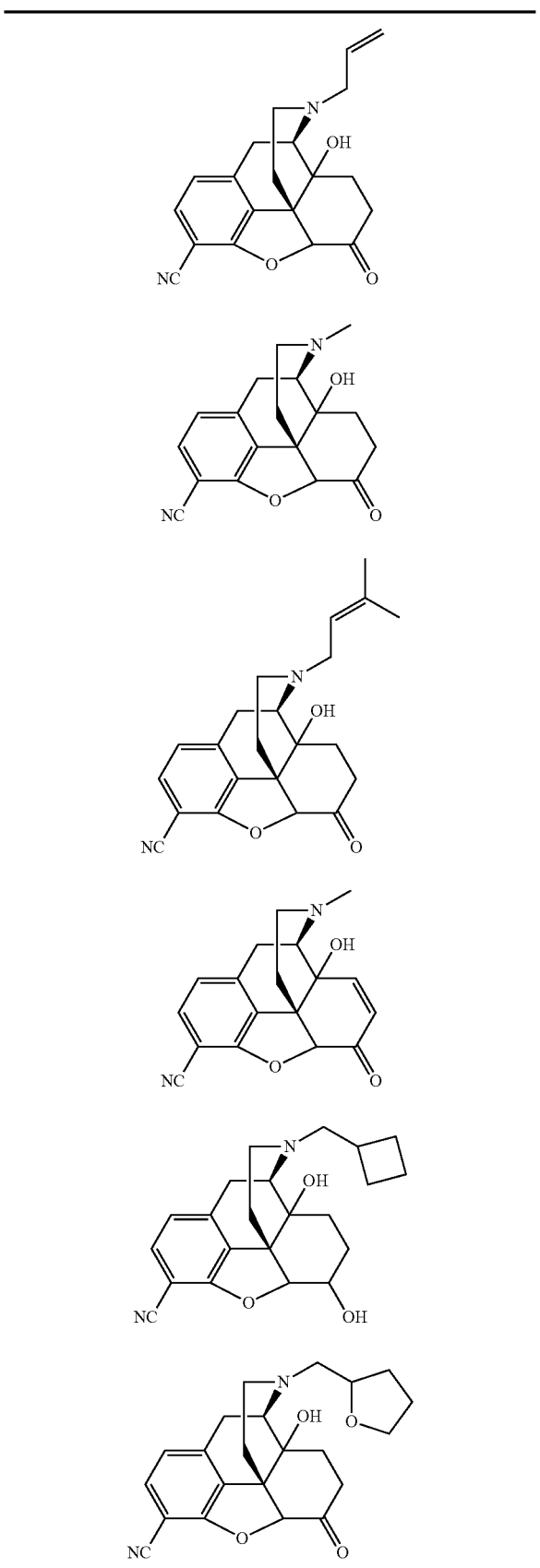
TABLE 6-continued
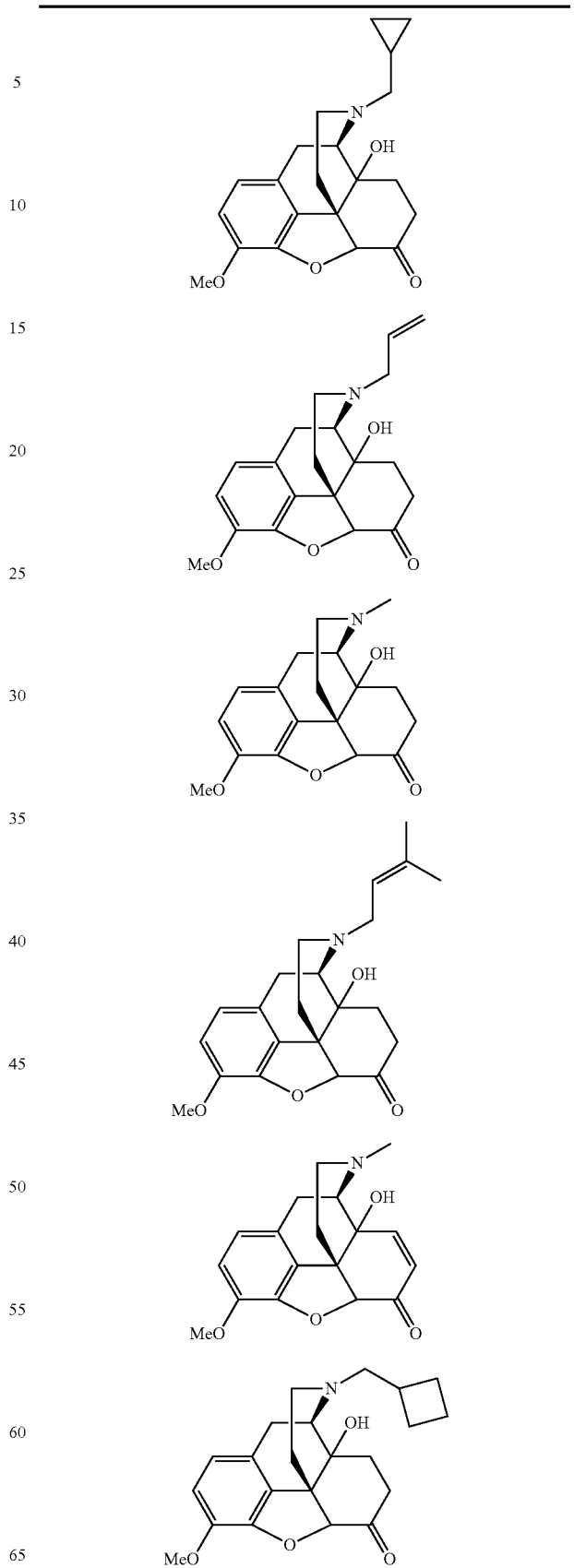

TABLE 6-continued

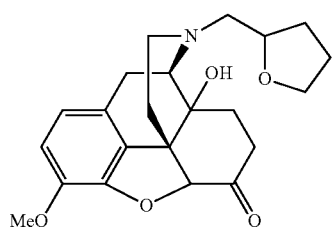 [SMILES: COc1ccc2c3c1OC1C(=O)CCC4(O)[C@@H](C2)N(CC2CCCO2)CC[C@]314]

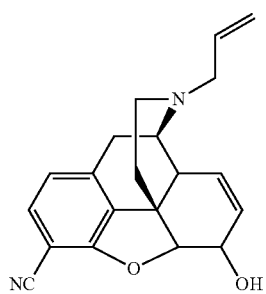 [SMILES: C=CCN1CC[C@]23c4c5ccc(C#N)c4OC2C(O)C=CC3[C@H]1C5]

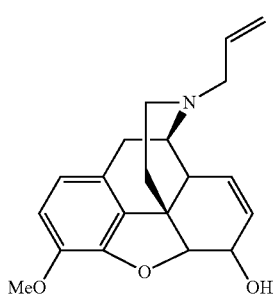

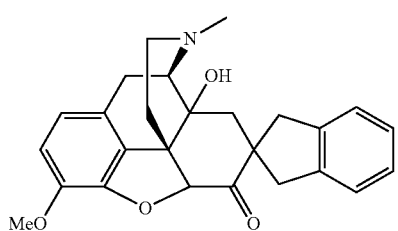 [SMILES: COc1ccc2c3c1OC1C(=O)C4(Cc5ccccc5C4)CC4(O)[C@@H](C2)N(C)CC[C@]314]

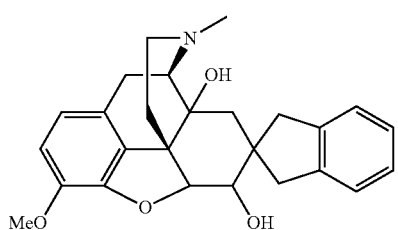 [SMILES: COc1ccc2c3c1OC1C(O)C4(Cc5ccccc5C4)CC4(O)[C@@H](C2)N(C)CC[C@]314]

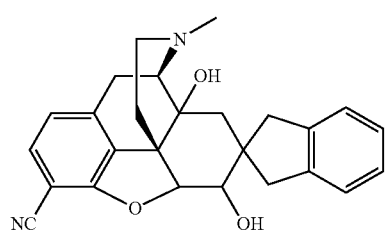 [SMILES: CN1CC[C@]23c4c5ccc(C#N)c4OC2C(O)C2(Cc4ccccc4C2)CC3(O)[C@H]1C5]

TABLE 6-continued

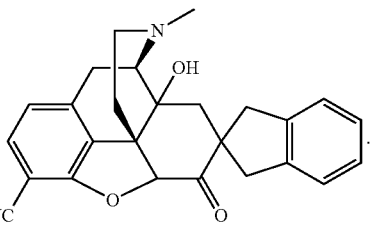

In one embodiment, the $R_{30}$ group of a compound of Formula IIB is converted to a hydroxyl group. In one embodiment, the $R_{30}$ group is —OMe and said methyl ether is converted to a hydroxyl group through demethylation. Demethylation can be accomplished by reacting a compound of Formula IIB with $BCl_3$, $BBr_3$, $SnO_2$, alkylthiolate anions, trialkylsilylhalides, dialylphosphide anions or alkali organomides such as $NaN(SiMe_3)$ and $LiN(i-Pr)_2$, The conversion of $R_{30}$ group of a compound of Formula IIB results in a compound of Formula IB. The compound of Formula IB can be further reacted with a triflating agent to give a compound of Formula IC as discussed above. The invention further relates to the synthesis of a compound of Formula ID by reacting a compound of Formula IC as discussed previously. The invention further relates to the synthesis of compounds of Formula IE and Formula I through hydrolysis of a compound of Formula ID. In a preferred embodiment, $R_{30}$ is —OMe. In a preferred embodiment, $R_1$ is selected from —$CH_3$, —$CH_2$-c-$C_3H_5$, —$CH_2$-c-$C_4H_7$, —$CH_2$—$CH=CH_2$, —$CH_2$—$CH=C(CH_3)_2$. The invention further provides a process for the synthesis of a compound of Formula IIIA:

Formula IIIA

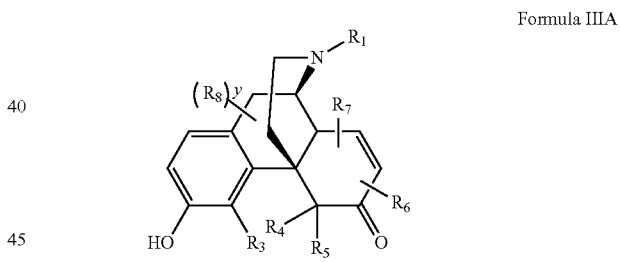

Comprising the step of reacting a compound of Formula IIIB with an acid, preferably an organic acid;

Formula IIIB

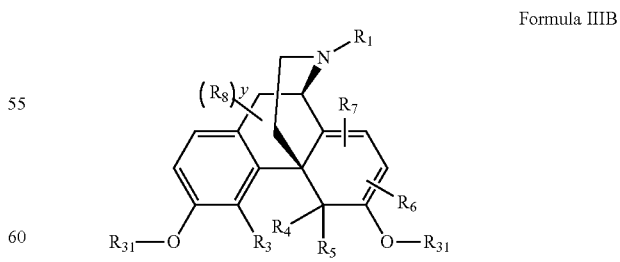

Wherein $R_{21}$ is an alkyl, substituted alkyl, aryl, or substituted aryl.

In a preferred embodiment, the organic acid is formic acid. In a preferred embodiment, the reaction is conducted in the presence of hydrogen peroxide. In a preferred embodiment, compound of formula IIIB is thebaine, and said compound of Formula IIIA is 14-hydroxycodeinone.

In one embodiment, the invention relates to a method of hydrogenating a compound of Formula IIIA to give a compound of Formula IIIC:

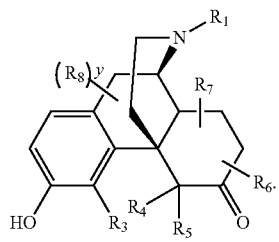

Formula IIIC

In a preferred embodiment, the hydrogenation is in the presence of Pd/C. In a preferred embodiment, the compound of Formula IIIA is 14-hydroxycodeinone, and said compound of Formula IIIC is oxycodone.

In one embodiment, the invention relates to a process for the synthesis of a compound of Formula IVB, comprising the step of reacting a compound of Formula IVA:

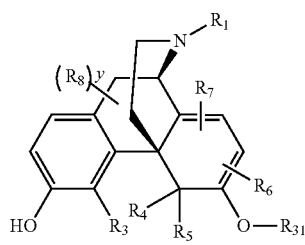

Formula IVA with a trifilating agent to give a compound of Formula IVB:

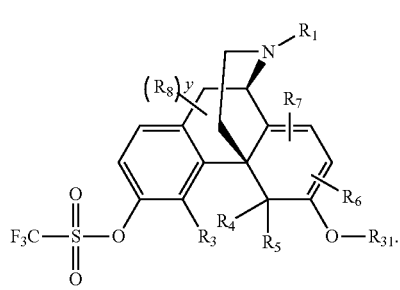

Formula IVB

In one embodiment, the invention relates to a method further comprising the step of reacting a compound of Formula IVB with a cyanide to produce a compound of Formula IVC:

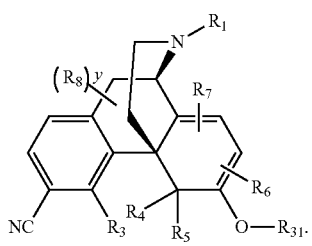

Formula IVC

The compound of formula IVC can be optionally reacted with an acid to give a compound of Formula IVD:

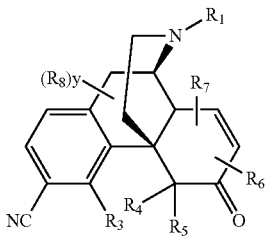

Formula IVD

The compound of IVD can be hydrogenated to give a compound of Formula IVE:

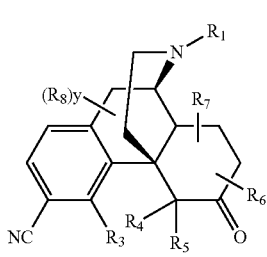

Formula IVE

The compound of Formula IVE can be reacted with a compound of formula:

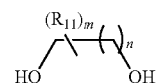

to give a compound of Formula ID.

In a preferred embodiment, the compound of Formula IVA is oripavine. In a preferred embodiment, $R_2$ is —$CONH_2$.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle", "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The phrase "minimum stirrable volume" refers to a solution or sludge that can be stirred with a stirrer or a paddle or a stirring device that has some amount of solvent still left in the mixture along with a solute. Generally, such solution/sludge results from evaporating/reducing a solvent in a solution where the reduction of solvent has not completely removed the solvent, but left the mixture in a reduced state where the mixture can be still stirred using a conventional method.

Substituents indicated as attached through variable points of attachments can be attached to any available position on the ring structure.

EXAMPLE

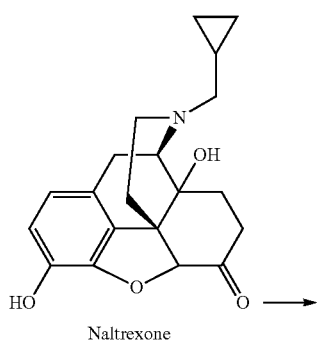

Naltrexone

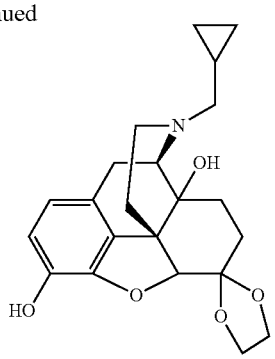

Compound-1

A reactor under inert atmosphere was charged with toluene (70 L), Naltrexone (7000 g), ethylene glycol (31.6 kg) followed by p-TsOH (4096 g). While stirring, the reaction mixture was heated to 108 to 110° C. and stirred for 3 to 18 hours. Upon reaction completion as determined by HPLC, to the reaction mixture was cooled to 18-20° C. The layers were separated and the bottom layer was transferred to a clean vessel. Purified water (125 L, 18 vol.) was added and cooled to 5 to 8° C. The pH was adjusted to 9-10 by adding solid sodium carbonate (Na$_2$CO$_3$) (2500 g). The suspension was stirred at room temperature for a minimum of 45 minutes and solid precipitates were isolated. The precipitates were washed with purified water and dried in vacuo at 30-35° C. to give Compound-1 (7561 g, 95% yield).

H$^1$NMR (400 MHz, D$_6$-DMSO): 8.78 (1H, br s), 6.41 (1H, d, 8.0 Hz); 6.30 (1H, d, 8.0 Hz); 4.80 (1H, br s); 4.22 (1H, s); 3.96-3.90 (1H, m); 3.83-3.76 (1H, m); 3.68-3.56 (2H, m); 2.90-2.79 (2H, m); 2.49-2.31 (2H, m); 2.35-2.15 (2H, m); 2.10-1.82 (3H, m); 1.35-1.25 (3H, m); 1.11-1.05 (1H, s); 0.75-0.65 (1H, m); 0.40-0.30 (2H, m); 0.05-(−) 0.05 (2H, m).

A reactor under inert atmosphere was charged with dichloromethane (DCM; 36 L) and Compound 1 (7200 g). The reaction was cooled to below −15° C. diisopropylethylamine (DEPEA; 3621 g) was slowly added to the reactor followed by Trifluoromethanesulfonic anhydride (Tf$_2$O; 5692 g). The reaction was mixture was kept between −15° C. and 0° C. with constant stirring for a minimum of 15 minutes. Upon reaction completion as determined by HPLC, the reactor was charged with 20% Ammonium chloride solution (43 L, 6 vol.) and methyl tertiary butyl ether (MTBE; 90 L). The reaction mixture was stirred for a minimum of 15 minutes and then layers were separated. The organic layer was washed with 20% Ammonium chloride solution (43 L, 6 vol.), followed by water (43 L, 6 vol.) and then brine (58 L, 8 vol.). The organic layer was treated with magnesium sulfate and charcoal. The solution was filtered and concentrated under vacuum to a minimum stirrable volume. A co-evaporation with MTBE (30 L) was performed followed by two with heptanes (2×30 L). The suspension was cooled to less than 10° C. and Compound 9 was isolated as a solid. The solids were washed with heptanes (10 L, 2 vol.) and dried in vacuo at 30-35° C. to give Compound 9 (8878 g, 88% yield).

H$^1$NMR (400 MHz, D$_6$-DMSO): 6.98 (1H, d, 8.4 Hz); 6.65 (1H, d, 8.4 Hz); 4.54 (1H, s); 3.92-3.86 (1H, m); 3.70-3.52 (4H, m); 2.97-2.91 (2H, m), 2.54-2.10 (3H, m); 1.96-1.86 (1H, m); 1.82-1.74 (1H, m); 1.36-1.20 (3H, m); 1.09-0.97 (1H, s); 0.74-0.68 (1H, m); 0.40-0.30 (2H, m); 0.04-(−) 0.03 (2H, m).

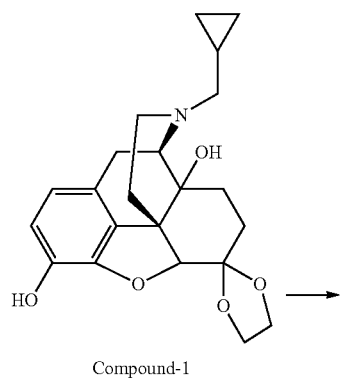

Compound-1

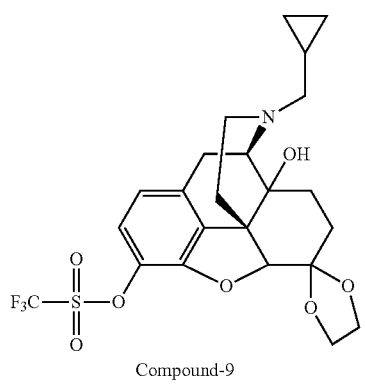

Compound-9

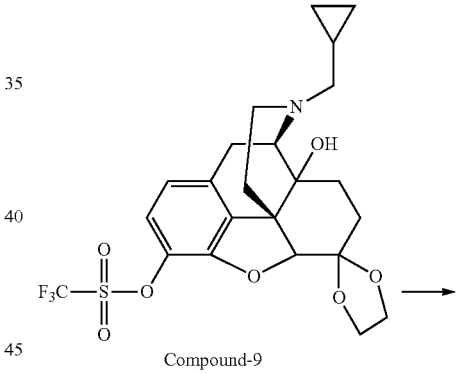

Compound-9

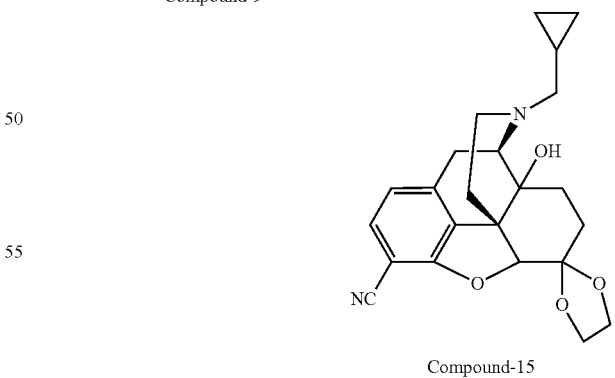

Compound-15

Under the inert atmosphere, a reactor was charged with N,N-dimethyl formamide (DMF; 48.5 L), Compound 9 (8800 g), Pd(OAc)$_2$ (191 g) followed by 1,1'-bis(diphenylphosphanyl) ferrocene (DPPF; 943 g). The reaction mixture was slowly heated to approximately 65° C. After the contents reached 65° C. zinc cyanide (1198 g) was added. The reaction was heated to 80° C. and stirred for a minimum of 1 hour. Upon reaction completion as judged by HPLC the reactor contents were cooled to less than 5° C. The reactor was charged with purified water (230 L, 30 vol.) followed by a controlled addition of aqua ammonia (15.5 L) to adjust the pH to 10.5 to 11. The suspension was warmed to >15° C. and solids were isolated. The isolated solids were washed with water (3×35 L) followed by heptanes (2×12 L). The solids were dried in oven at 30-35° C. until constant weight is reached. The crude solids were suspended in ethanol. The suspension is heated to 65° C. The suspension is then cooled to below 20° C. The solids are isolated by filtration and washed with ethanol (3×0.5 vol. of solids isolated). Dry the solids in a vacuum oven and dry at 30-35° C. constant weight is reached to provide Compound 15 (8878 g, 88% yield).

Elemental Analysis: C, 69.34%; H, 6.55%; N, 7.08%; (Expected: 70.03, 6.64, 7.10).

H$^1$NMR (400 MHz, CDCl$_3$): 7.24 (1H, d, 8 Hz), 6.72 (1H, d, 8 Hz); 5.01 (1H, s); 4.72 (1H, s); 4.23-4.18 (1H, m); 4.00-3.88 (2H, m); 3.81-3.77 (1H, m); 3.13 (1H, d, 5.4 Hz); 3.14-3.05 (2H, m); 2.70-2.60 (2H, m); 2.4-2.2 (4H, m); 2.02 (1H, dt, 11.6, 3.3 Hz); 1.63-1.35 (4H, m); 0.9-0.8 (1H, m); 0.55 (2H, d, 7.5 Hz); 0.13 (2H, d, 7.5 Hz).

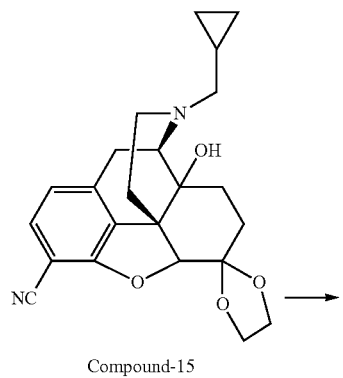

Compound-15

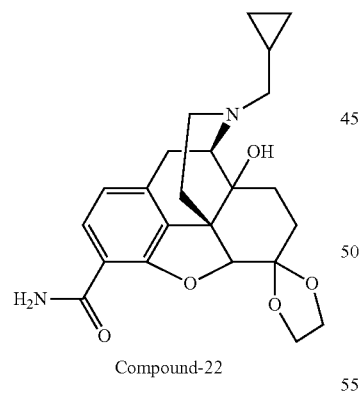

Compound-22

A reaction vessel under inert atmosphere was charged with t-Butanol (60 L), sodium chloride (12 kg) and Compound 15 (6000 g). Potassium hydroxide (KOH; 2986 g) was added and the reaction mixture was heated to 8° C. Upon reaction completion as judged by HPLC, the reaction mixture was cooled to 20° C. to 30° C. 2-Methyltetrahydrofuran (2-Me-THF; 72 L, 12 vol.) was added to the reaction mixture. The reactor was charged with 15% brine solution (60 L) and stirred for a minimum of 20 minutes. The layers were separated and the aqueous layer was further extracted with 2-Me-THF (30 L, 5 vol.). The organic layers were combined and washed three times with 15% brine solution (48 L, 8 vol.). The organic layer was treated with magnesium sulfate followed by charcoal. The solution was filtered and concentrated under vacuum to a minimum stirrable volume. Two co-evaporations with MTBE (2×24 L) followed by two with Heptanes (2×24 L) were performed. The resulting suspension was cooled to less than 10° C. The suspension was filtered and washed with heptanes (12 L, 2 vol.). The solid products were dried in a vacuum oven at 30-35° C. to give Compound 22 (5050 g, 82% yield).

H$^1$NMR (400 MHz, D$_6$-DMSO): 7.55 (1H, d, 8 Hz), 7.47 (1H, s); 7.01 (1H, s); 6.76 (1H, d, 8 Hz); 4.99 (1H, dd, 13.5, 5.8); 3.80 (1H, dd, 13.7, 7); 3.72-3.66 (2H, m); 3.09-3.04 (2H, m); 2.68-2.56 (2H, m); 2.40-2.20 (3H, m); 2.10-2.00 (1H, m); 1.96-1.84 (1H, m); 1.50-1.34 (3H, m); 1.24-1.18 (1H, m); 0.9-0.8 (1H, m); 0.52-0.42 (2H, m); 0.17-0.07 (2H, m).

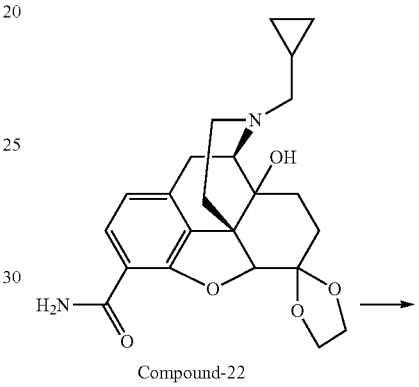

Compound-22

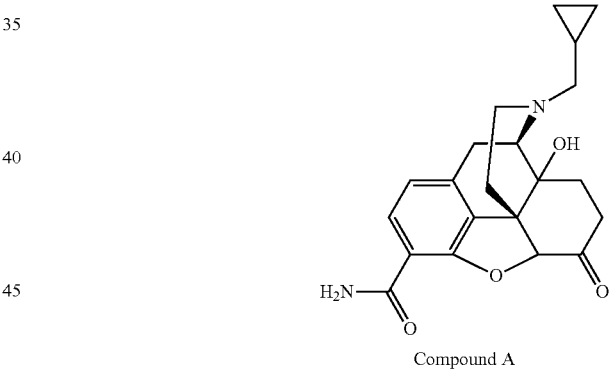

Compound A

A reaction vessel under inert atmosphere was charged with reverse osmosis/deionized water (75 L) and Hydrochloric acid, 37% ACS grade (8 L). The contents were cooled and Compound 22 (5000 g) and Toluene (50 L) were added. The biphasic mixture was heated to 80° C. Upon reaction completion as judged by HPLC, the reaction mixture was cooled to 15° C. to 20° C. The layers were separated and dichloromethan (DCM; 25 L) was added to the aqueous layer and the mixture was stirred for a minimum of 15 minutes. Separate the layers and filter the aqueous mixture into a clean vessel and cool the filtrate to 0° C. The pH of the reaction mixture was adjusted to 9 to 10 by charging the reaction vessel with aqueous Ammonia. The resulting suspension was stirred to below 20° C. for a minimum of 45 minutes. The solids were isolated by filtration and washed with water (4×15 L). The solids were dried in a vacuum oven at 30-35° C. to provide Compound-A (3592 g, 80% yield).

H$^1$NMR (400 MHz, D$_6$-DMSO): 7.66 (1H, s); 7.56 (1H, d, 7.8 Hz), 7.11 (1H, s); 6.85 (1H, d, 8.2 Hz); 5.26 (1H, br s); 5.16 (1H, s); 3.19 (1H, d, 6.4 Hz); 3.14 (1H, s); 3.09 (1H, s); 3.03-2.94 (1H, m); 2.70-2.61 (2H, m), 2.51-2.33 (3H, m); 2.15-2.11 (1H, m); 1.96-1.88 (1H, m); 1.85-1.78 (1H, m); 1.47-1.32 (2H, m); 0.94-0.84 (1H, m); 0.54-0.44 (2H, m); 0.18-0.08 (2H, m).

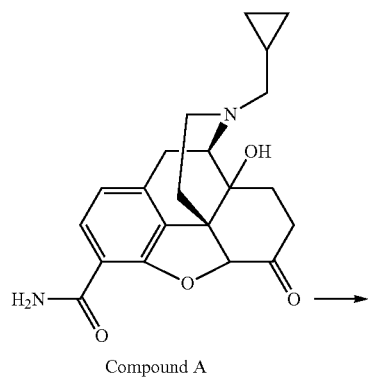

Compound A

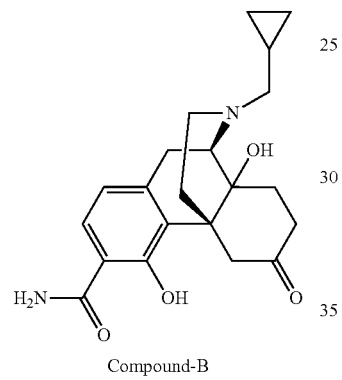

Compound-B

A method for converting Compound-A to Compound-B is disclosed in U.S. Pat. No. 7,262,298 which is adopted as described below.

A reaction vessel under inert atmosphere was charged with 200 proof ethanol (52.5 L) and Compound-A (3500 g). Ammonium chloride (NH$_4$Cl, 1776 g) and Zinc dust, <10 micron (2234 g) were added and the reaction mixture was heated to 60-63° C. Upon reaction completion as judged by HPLC, reaction mixture was cooled to 18° C. to 22° C., filtered, and concentrated under vacuum to a minimum stirrable volume. Two co-evaporations with 2-Me-THF (2×15 L) to a minimum stirrable volume. The reaction mixture was cooled to 15° C. to 18° C. and 2-Me-THF was added followed by aqua ammonia to adjust the pH of the reaction mixture to 9.0-10.0. The reactor was charged with water (60 L) and MTBE (7 L). The layers were separated and the aqueous layer was further extracted with 2-Me-THF (15 L, 4.5 vol.)/MTBE (3.5 L). The combined organic layers were washed with a brine solution (35 L, 10 vol.). The organic layer was dried with magnesium sulfate, followed by addition of charcoal. The solution was filtered and treated with 3-mercaptopropyl silica gel (Si-Thiol). Remove the solids and concentrate the filtrate under vacuum to a minimum stirrable volume. Two co-evaporations were performed with MTBE (4 vol.) followed by two co-evaporations with Heptanes (4 vol.) to a minimum stirrable volume. The reaction mixture was cooled to 15-18° C. and charged with Heptanes (7 L). The suspension was cooled to <10° C. and stirred for minimum of 1.5 hours. The suspension was filtered, washed with heptanes and dried in a vacuum oven at 30-35° C. to give Compound-B (3090 g, 90% yield).

Elemental Analysis: C, 68.35%; H, 7.06%; N, 7.47%; (Theory: 68.09, 7.07, 7.56)

H$^1$NMR (400 MHz, CDCl$_3$): 13.2 (1H, s); 7.12 (1H, d, 8.2 Hz), 6.50 (1H, d, 9 Hz); 6.10 (2H, br s); 4.70 (1H, s); 4.05 (1H, d, 11.3 Hz); 3.12 (1H, d, 6.3 Hz); 3.00-2.95 (2H, m); 2.90-2.77 (2H, m), 2.67-2.62 (1H, m); 2.36 (2H, d, 6.4 Hz); 2.2-1.8 (5H, m); 1.75-1.68 (1H, m); 0.9-0.8 (1H, m); 0.58-0.51 (2H, m); 0.15-0.10 (2H, m).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound selected from Table 3:

TABLE 3

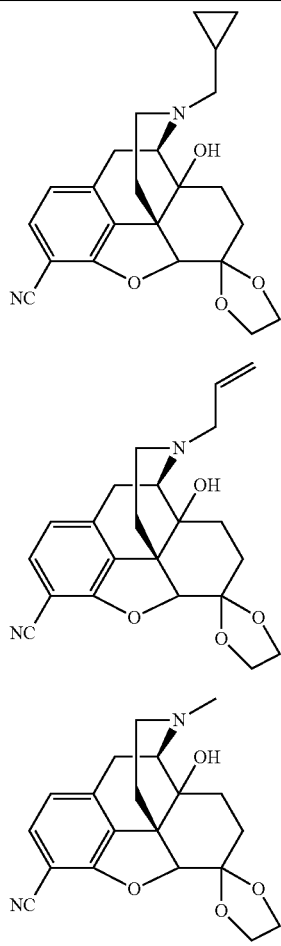

TABLE 3-continued
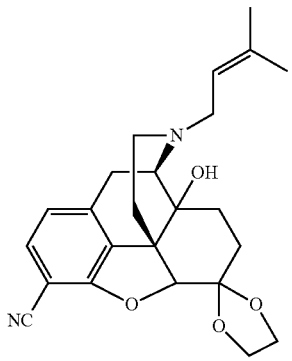 [SMILES: CC(C)=CCN1CC[C@]23c4c5ccc(C#N)c4OC2C2(CCC3(O)[C@H]1C5)OCCO2]
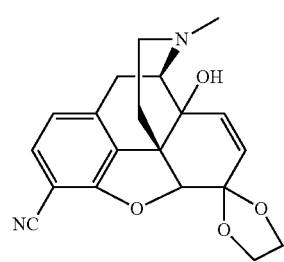 [SMILES: CN1CC[C@]23c4c5ccc(C#N)c4OC2C2(C=CC3(O)[C@H]1C5)OCCO2]
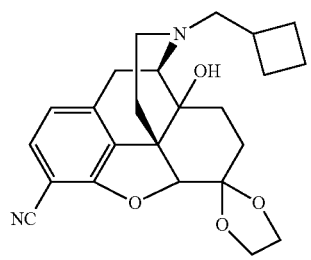 [SMILES: N#Cc1ccc2c3c1OC1C4(CCC5(O)[C@@H](C2)N(CC2CCC2)CC[C@]315)OCCO4]
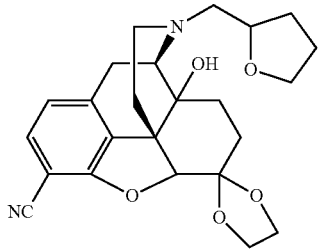
2. A compound of formula:
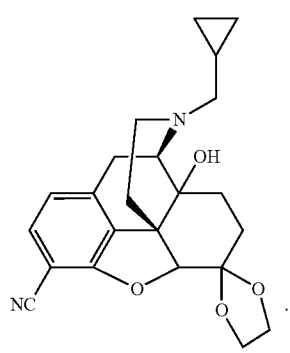 [SMILES: N#Cc1ccc2c3c1OC1C4(CCC5(O)[C@@H](C2)N(CC2CC2)CC[C@]315)OCCO4]
3. A compound of formula:
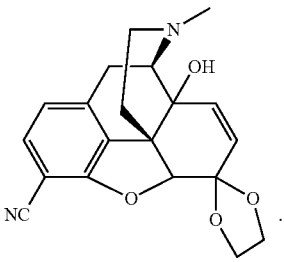 [SMILES: CN1CC[C@]23c4c5ccc(C#N)c4OC2C2(C=CC3(O)[C@H]1C5)OCCO2]
4. A compound of formula:
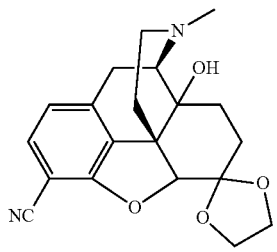
5. A compound of formula:
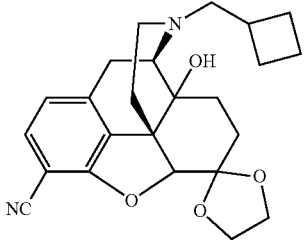
6. A compound of formula:
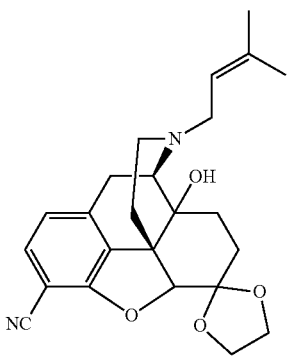

7. A compound of formula:
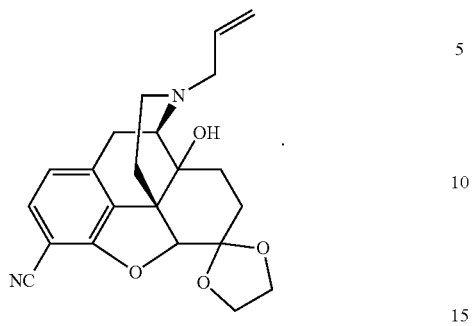
8. A compound of formula:
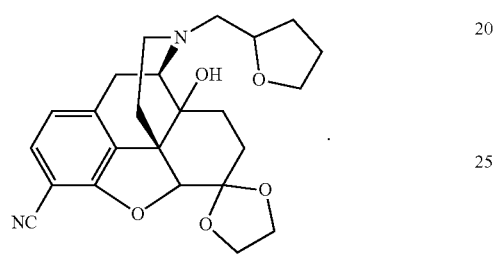
* * * * *